United States Patent
Magee (10) Patent No.: US 11,857,402 B1
(45) Date of Patent: Jan. 2, 2024

(54) OSMOTIC SANITARY COLLECTION BAG

(71) Applicant: Florida A&M University, Tallahassee, FL (US)

(72) Inventor: Charles Magee, Cairo, GA (US)

(73) Assignee: Florida A&M University, Tallahassee, FL (US)

( * ) Notice: Subject to any disclaimer, the term of this patent is extended or adjusted under 35 U.S.C. 154(b) by 827 days.

(21) Appl. No.: 16/697,459

(22) Filed: Nov. 27, 2019

Related U.S. Application Data (60) Provisional application No. 62/778,063, filed on Dec. 11, 2018.

(51) Int. Cl.
   *A61F 13/551* (2006.01)
   *A61F 13/15* (2006.01)
   (Continued)

(52) U.S. Cl.
   CPC .... *A61F 13/5515* (2013.01); *A61F 13/15203* (2013.01); *A61F 13/49* (2013.01);
   (Continued)

(58) Field of Classification Search
   CPC ............ A61F 13/8405; A61F 13/51104; A61F 13/49003; A61F 13/505; A61F 13/47272; A61F 13/4722; A61F 13/47218; A61F 13/47209; A61F 13/472; A61F 13/2057; A61F 13/2045; A61F 13/202; A61F 13/20; A61F 13/15268; A61F 13/84; A61F 13/82; A61F 13/70; A61F 13/5644; A61F 13/5611; A61F 13/5605; A61F 13/5519; A61F 13/5516; A61F 13/15; A61F 2013/4956; A61F 2013/47281; A61F 2013/4729; A61F 2013/16; A61F 2013/8426; A61F 2013/8417;
   (Continued)

(56) References Cited

U.S. PATENT DOCUMENTS 514,717 A * 2/1894 Kirwin .................. A61F 5/4553
                                                    604/354
3,814,101 A * 6/1974 Kozak .................... A61L 15/24
                                                    604/366
(Continued)

FOREIGN PATENT DOCUMENTS

CN          100418586 C  *  9/2008   ............. A61L 15/60

OTHER PUBLICATIONS

NPL search history (Year: 2022).*

*Primary Examiner* — Nicholas J. Weiss
*Assistant Examiner* — Gabriella E Burnette
(74) *Attorney, Agent, or Firm* — Owen G. Behrens; Smith & Hopen, P.A.

(57) ABSTRACT

An osmotic sanitary collection bag for collecting fluid discharged from the vagina during menstruation. The osmotic sanitary collection bag includes an absorbent sponge having a plurality of drainage apertures disposed therethrough. Elongated adhesive strips extend away from the sponge and are adhered to a first surface of a conventional sanitary device to secure the osmotic sanitary collection bag in place. A collection bag abuts the absorbent sponge and is disposed in underlying relation to the absorbent sponge and the drainage apertures. The absorbent sponge is laced with salt, alcohol, and an odor-masking substance, such as sodium bicarbonate.

18 Claims, 6 Drawing Sheets

(51) Int. Cl.
*A61F 13/49* (2006.01)
*A61F 13/512* (2006.01)
*C01D 7/00* (2006.01)
*A61F 13/53* (2006.01)
*A61F 13/84* (2006.01)
*A61F 13/539* (2006.01)

(52) U.S. Cl.
CPC .. *A61F 13/512* (2013.01); *A61F 2013/15463* (2013.01); *A61F 2013/15528* (2013.01); *A61F 2013/530802* (2013.01); *A61F 2013/53908* (2013.01); *A61F 2013/55155* (2013.01); *A61F 2013/8414* (2013.01); *C01D 7/00* (2013.01)

(58) Field of Classification Search
CPC ...... A61F 2013/8414; A61F 2013/8408; A61F 6/08; A61F 5/44
See application file for complete search history.

(56) References Cited

U.S. PATENT DOCUMENTS

| | | | | |
|---|---|---|---|---|
| 4,031,897 A * | 6/1977 | Graetz | ............... | A61F 5/455 604/397 |
| 4,467,806 A * | 8/1984 | Bhiwandiwala | .... | A61F 13/2051 606/193 |
| 4,950,262 A * | 8/1990 | Takagi | ............ | A61F 13/5116 604/385.101 |
| 5,009,649 A * | 4/1991 | Goulter | ............ | A61F 5/453 604/351 |
| 5,122,407 A * | 6/1992 | Yeo | ............ | A61L 15/20 442/76 |
| 5,545,156 A * | 8/1996 | DiPalma | ............ | A61F 13/51401 604/378 |
| 5,849,003 A * | 12/1998 | Olsen | ............ | A61F 13/47218 604/385.03 |
| 6,113,582 A * | 9/2000 | Dwork | ............ | A61F 5/453 604/351 |
| 7,125,401 B2 * | 10/2006 | Yoshimasa | ......... | A61F 13/5605 604/385.03 |
| 9,980,856 B2 * | 5/2018 | Wilson | ............ | A61F 13/474 |
| 10,507,259 B2 * | 12/2019 | Cree | ............ | A61L 15/58 |
| 10,835,426 B2 * | 11/2020 | Coffman | ............ | A61F 13/47218 |
| 2003/0208112 A1* | 11/2003 | Schmidt | ............ | A61F 5/451 600/313 |
| 2007/0049891 A1* | 3/2007 | Clark | ............ | A61F 13/5513 604/385.13 |
| 2008/0221541 A1* | 9/2008 | Lavash | ............ | A61F 13/47218 604/385.01 |
| 2014/0243779 A1* | 8/2014 | Kim | ............ | A61F 13/82 604/401 |
| 2015/0202090 A1* | 7/2015 | Shalon | ............ | A61F 13/66 604/385.03 |
| 2016/0302978 A1* | 10/2016 | Lindström | ............ | A61F 13/625 |
| 2016/0324696 A1* | 11/2016 | Cree | ............ | A61L 15/425 |
| 2018/0014982 A1* | 1/2018 | Koulai | ............ | A61F 13/47272 |
| 2020/0222253 A1* | 7/2020 | Roszkowiak | ......... | A61F 13/539 |

* cited by examiner

OSMOTIC SANITARY COLLECTION BAG

CROSS-REFERENCE TO RELATED APPLICATIONS

This non-provisional application is a continuation of and claims priority to provisional application No. 62/778,063, entitled "OSMOTIC SANITARY COLLECTION BAG," filed Dec. 11, 2018 by the same inventor.

BACKGROUND OF INVENTION

1. Field of the Invention

This invention relates, generally, to sanitary pads. More specifically, it relates to a reusable sanitary collection bag for attachment to conventional sanitary pads.

2. Brief Description of the Prior Art

At least once a month, during menstruation, millions of women leave home concerned about leaks from their conventional sanitary pads—many times due to the unpredictability of their menstrual flow. Other individuals are also worried about their incontinence pad or absorbent underwear leaking or giving off an unpleasant odor from the discharged bodily fluids. Typically, menstrual leaks occur during periods of heavy flow and when sanitary pads are too small, too thin, or incorrectly positioned on the wearer's underwear. At night, women tend to use larger and thicker sanitary pads to absorb the heavy flow of blood and fluids discharged during menstruation. At times, females may place a towel on the bedsheet to prevent stains if the sanitary pad does leak.

Stains on clothes and sheets can also result from vaginal discharges commonly due to yeast infections and bacterial vaginosis. Yeast is a fungus typically present in and around the female genitals in relatively small numbers. When an event occurs that changes the balance of these organisms, the number of yeast cells can multiply leading to infection. Yeast infections affect up to 75% of women at some point during their lifetime and are most commonly caused by *Candida albicans*. The main symptom of a vaginal yeast infection is itching; however, burning, discharge, and pain during urination or intercourse may also occur.

Presently, no sanitary pads or underwear completely prevents leaks or infections during proper use. Foul odors are also associated with conventional sanitary devices because the devices provide an optimal environment for bacteria and fungi growth. This optimal environment can result in several ailments—such as rashes, yeast infections, and bacterial vaginosis.

Beyond leaking, there are several additional problems associated with conventional sanitary devices. Most poor women, especially those living in developing countries, cannot afford to buy one-time use pads or expensive anti-leak underwear. As a result, many women have resorted to cutting conventional sanitary devices in half to have twice as many pads. However, this practice only functions to exacerbate the problems associated with conventional sanitary devices.

Accordingly, what is needed is a sanitary pad or device that prevents or reduces leaks, odors, and infections resulting from bacteria and fungi growth, while being simple-to-use and cost-effective. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an osmotic sanitary collection bag having an absorbent sponge; a collection bag, and a plurality of adhesive strips for the collection and sanitation of bodily fluids is now met by a new, useful, and nonobvious invention.

The novel structure includes an osmotic sanitary collection bag (hereinafter "sanitary device") for use in absorbing a fluid (e.g., blood, urine, vaginal mucus, and tissue) discharged from a user. In an overlying relation, the sanitary device couples to a conventional sanitary device or underwear. The sanitary device includes an absorbent sponge having a first surface, a second surface, and a body extending therebetween. Disposed within the body of the absorbent sponge, a plurality of drainage apertures extends from a first surface to a second surface. An amount of salt is infused within the absorbent sponge and configured to facilitate, via osmosis, movement of the fluid discharged from the user to a collection bag.

Furthermore, the salt is a natural bactericide and kills any bacterial cells before colonization. Thus, the salt prevents the bacterial cells from reentering the vagina and causing an infection. In an embodiment, the sponge may be infused with an amount of alcohol to sanitize the absorbent sponge further and an amount of an odor-masking compound, such as sodium bicarbonate, to prevent or reduce odors.

The collection bag is disposed in underlying relation to the absorbent sponge and secured using an adhesive. The absorbent sponge may be disposed within at least a portion of a reservoir and configured to absorb fluids discharged from the user. Once absorbed, the fluids flow through the plurality of drainage apertures and collect within the reservoir.

Positioned in underlying relation to the absorbent sponge, the first and second plurality of adhesive strips extend away from an end of the absorbent sponge at a predetermined distance. An impermeable separation strip is disposed between each adhesive strip of the first and second plurality of adhesive strips and configured to facilitate the separation of each adhesive strip from one another. Additionally, the separation strip provides a waterproof seal over the adhesive to prevent the adhesive from being removed when the sanitary device is cleaned for reuse.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It is an object of the current invention to provide a sanitary device that prevents or reduces leaks, odors, and infections resulting from bacterial and fungal growth; is simple and easy to install in traditional pads or underwear; is re-useable and washable; is small in size; is low in cost; and is easy to store or dispose of. In an embodiment, the current invention is a sanitary device that can be used to prevent or reduce leaks, odors, and infections during female menstrual cycles.

In an embodiment, the sanitary device can absorb discharged fluids from the body due to bladder leaks in men, women, and children.

Figure 1A:
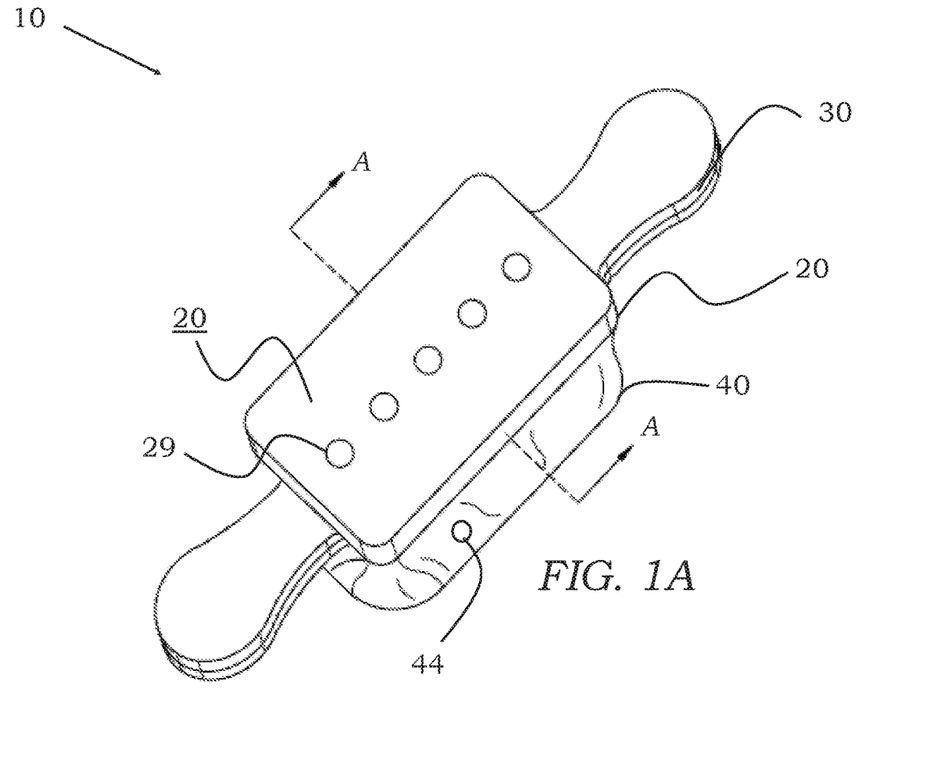
FIG. 1A is a perspective view of a sanitary device for sanitary pads/napkins, pantyliners, incontinence pads, and absorbent underwear, according to certain embodiments of the current invention.
Figure 1B:
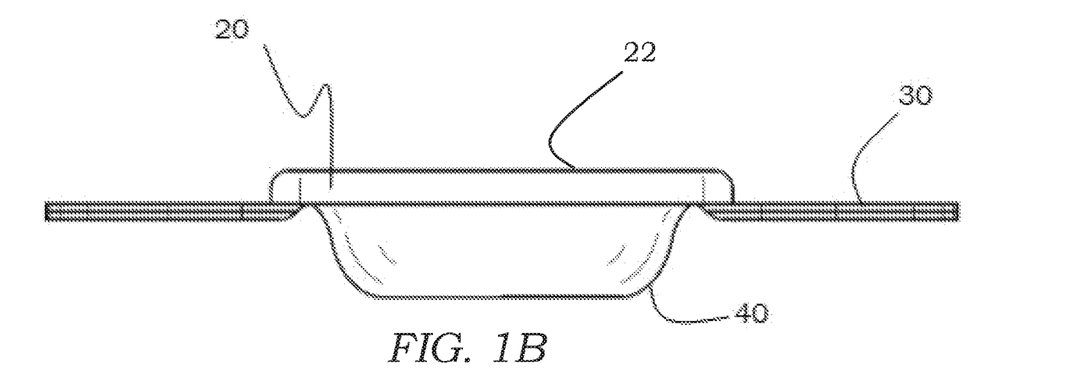
FIG. 1B is a side view of the sanitary device of FIG. 1.

As depicted in FIGS. 1A and 1B, sanitary device 10 comprises absorbent sponge 20, adhesive strips 30, and collection bag 40. Sanitary device 10 is smaller in overall size and lower in cost compared to conventional sanitary devices 15 on the market. Conventional sanitary devices 15 include tampons, sanitary napkins, sanitary towels, menstrual pads, or other devices for absorbing fluids discharged from the human body (see FIGS. 4A and 4B). In certain embodiments, conventional sanitary devices 15 may further include absorbent underwear, diapers, and adult diapers (see FIG. 4C).

Figure 2A:
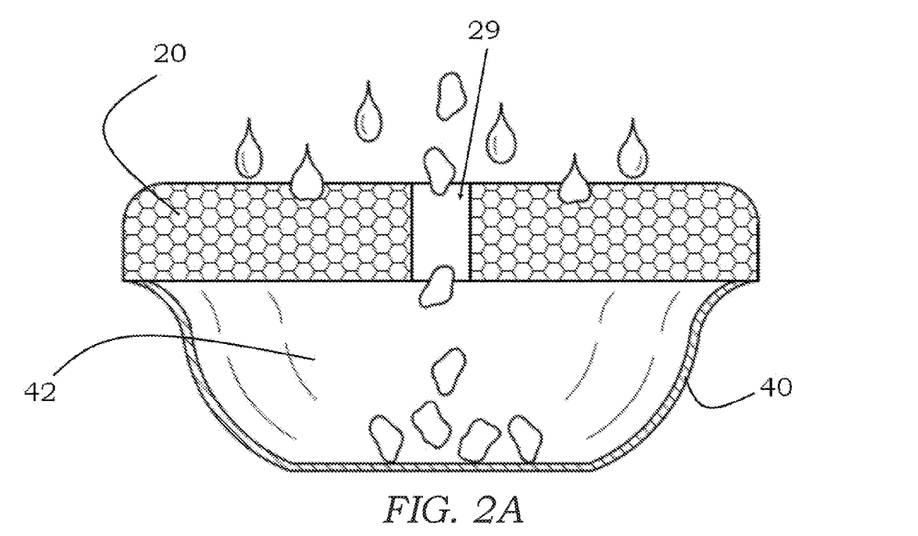
FIG. 2A is a cross-sectional view of the sanitary device taken along line A-A in FIG. 1A.

During use, sanitary device 10 is positioned centrally over the vaginal opening with upper portion 22 of absorbent sponge 20 pressed against the labia. Absorbent sponge 20 may be a variety of geometric shapes and configurations, including rectangular, square, and circular. When absorbent sponge 20 becomes saturated with fluids during menstruation, as depicted in FIG. 2A, the fluids drain in collection bag 40 through drainage aperture 29 disposed within the body of absorbent sponge 20. Drainage aperture 29 may be a single drainage aperture 29 or may include one or more drainage apertures 29 arranged in a pattern or randomly spaced apart from one another about absorbent sponge 20.

Figure 2B:
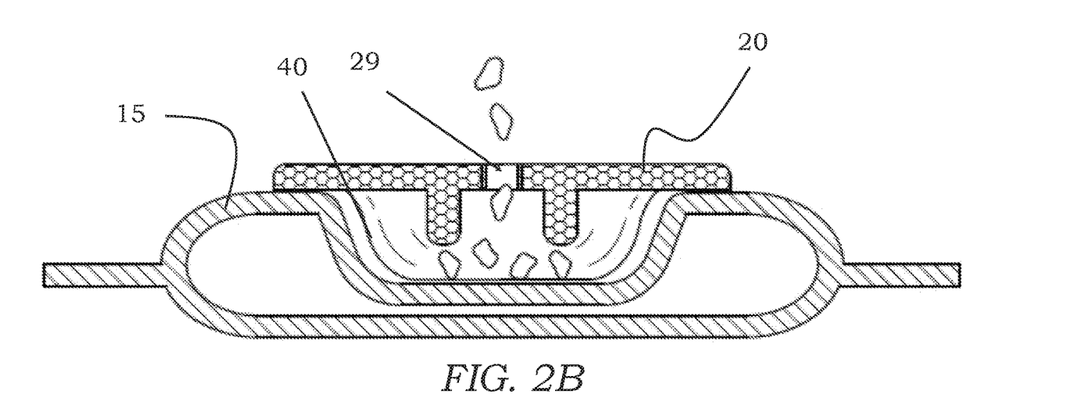
FIG. 2B is a cross-sectional view of the sanitary device taken along line B-B in FIG. 4A.

Collection bag 40 is disposed in underlying relation to absorbent sponge 20 and secured thereto using an adhesive, stitching, or other known coupling methods. At least a portion of absorbent sponge 20 may reside within collection bag 40, as depicted in FIG. 2B. For cost, impermeability, reusability, and durability reasons, collection bag 40 is ideally constructed from plastic. However, one of ordinary skill in the art would appreciate that collection bag 40 may be constructed from nylon, synthetic fiber, elastane, rubber, polyester, or other material and/or combination of materials suitable for containing fluids within reservoir 42. Collection bag 40 may include discharge mechanism 44 (e.g., plug), configured to drain the fluids within reservoir 42 once the reservoir is filled with fluids. In an embodiment, collection bag 40 of sanitary device 10 is configured to reside within the deepest groove of conventional sanitary pad 15. The groove is sized and shaped to receive collection bag 40 and prevent the collection bag from being displaced horizontally causing misalignment or discomfort.

The osmotic process dictates that a solution with a higher chemical potential will spontaneously diffuse into a solution with a lower chemical potential to achieve homeostasis. Further, the laws of physics dictate that a fluid will always seek and take the path of least resistance. Thus, absorbent sponge 20 is laced with an amount of salt. The salt allows for the migration of menstrual fluids—which have a higher chemical potential—to the salt-laced sponge having a lower chemical potential. This migration of fluids away from the vagina is quicker than that of conventional sanitary devices as a result of the chemical potential created by the salty environment. The rapid migration of menstrual fluids away from the opening of the vagina significantly reduces the potential for infection and other adverse medical conditions.

A healthy vagina has a large number of bacterial cells, while only a small number of yeast cells. The most common bacteria, *Lactobacillus acidophilus*, helps to keep various organisms, such as yeast cells, in check. Several medical issues, including vaginal yeast infections, can arise as the result of unchecked yeast growth. For example, a vaginal yeast infection is an indication that an overabundance of yeast cells are growing in or around the vagina. The chance of contracting a vagina yeast infection increases during menstrual periods as females are currently required to use convention sanitary pads. The use of conventional sanitary devices results in a warm and bloody environment close to the opening of the vagina, which facilitates bacteria and yeast colonization that leads to a number of adverse medical conditions.

In an embodiment, an amount of alcohol and/or odor masking compound may saturate absorbent sponge 20 to prevent the build-up bacteria and yeast colonization. In such embodiments, alcohol sanitizes and kills both bacterial and yeast cells upon the absorption of menstrual fluids by the sponge. The odor masking compound may be sodium bicarbonate or other similar compounds configured to remove an odor given off by menstrual or other bodily fluids. The combination of salt and alcohol destroys bacteria and yeast cells before they have the opportunity to colonize and reenter the vagina. Reentry into the vagina can result in an imbalance of bacteria within or around the vagina and potentially results in medical conditions, such as bacterial vaginosis. Further, an excess of bacteria and yeast on and around the labia can form a rash or build-up of yeast resulting in uncomfortable vaginal itching.

Figure 3A:
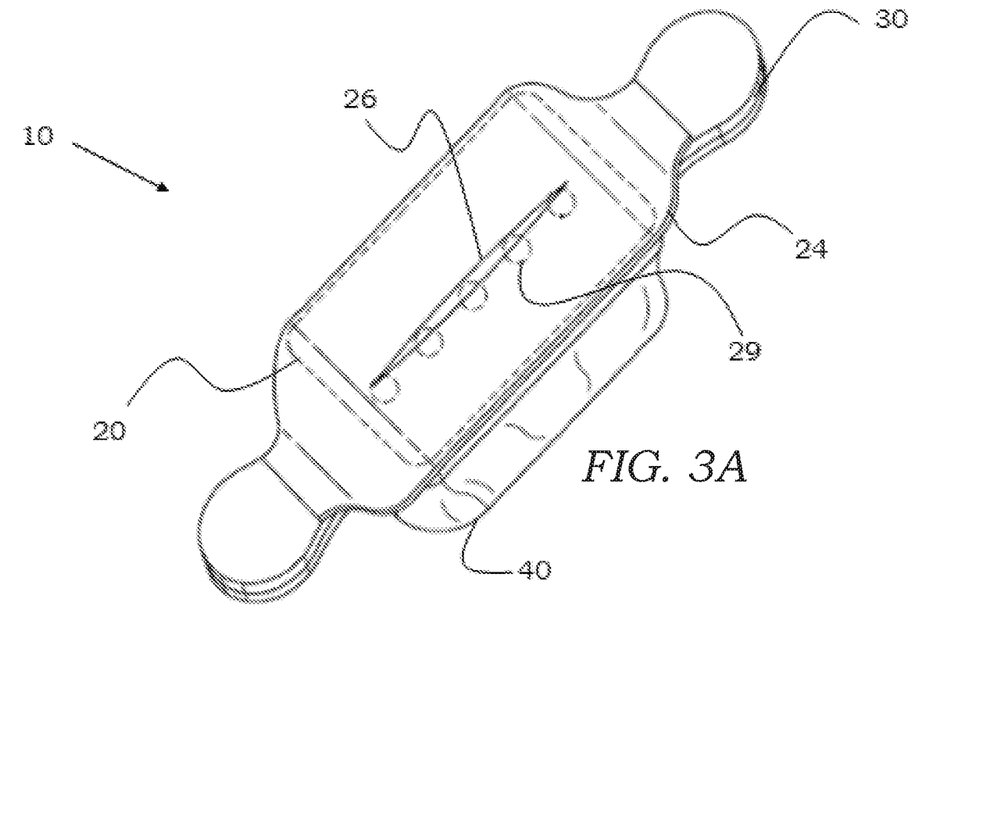
FIG. 3A is a perspective view of an embodiment of a sanitary device having a semi-permeable membrane disposed over the absorbent sponge.
Figure 3B:
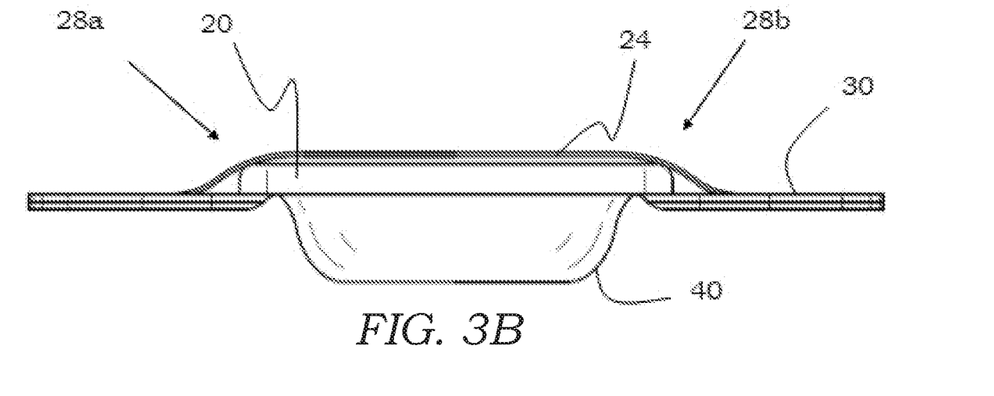
FIG. 3B depicts a side view of the embodiment of the sanitary device of FIG. 3A.

FIGS. 3A and 3B depict an embodiment having semi-permeable membrane 24 disposed over absorbent sponge 20. Semi-permeable membrane 24 prevents the salt distributed within absorbent sponge 20 from contacting the epidermis of the wearer. Pores formed within semi-permeable membrane 24 are sized small enough that the salt particles are unable to pass through, but large enough to permit the passage of fluids through semi-permeable membrane 24. As shown in FIG. 3A, slit 26 may be formed within semi-permeable membrane 24 to allow larger particles—such as vaginal tissue or clotted blood—to pass through the membrane and into reservoir 42 of collection bag 40.

Figure 4A:
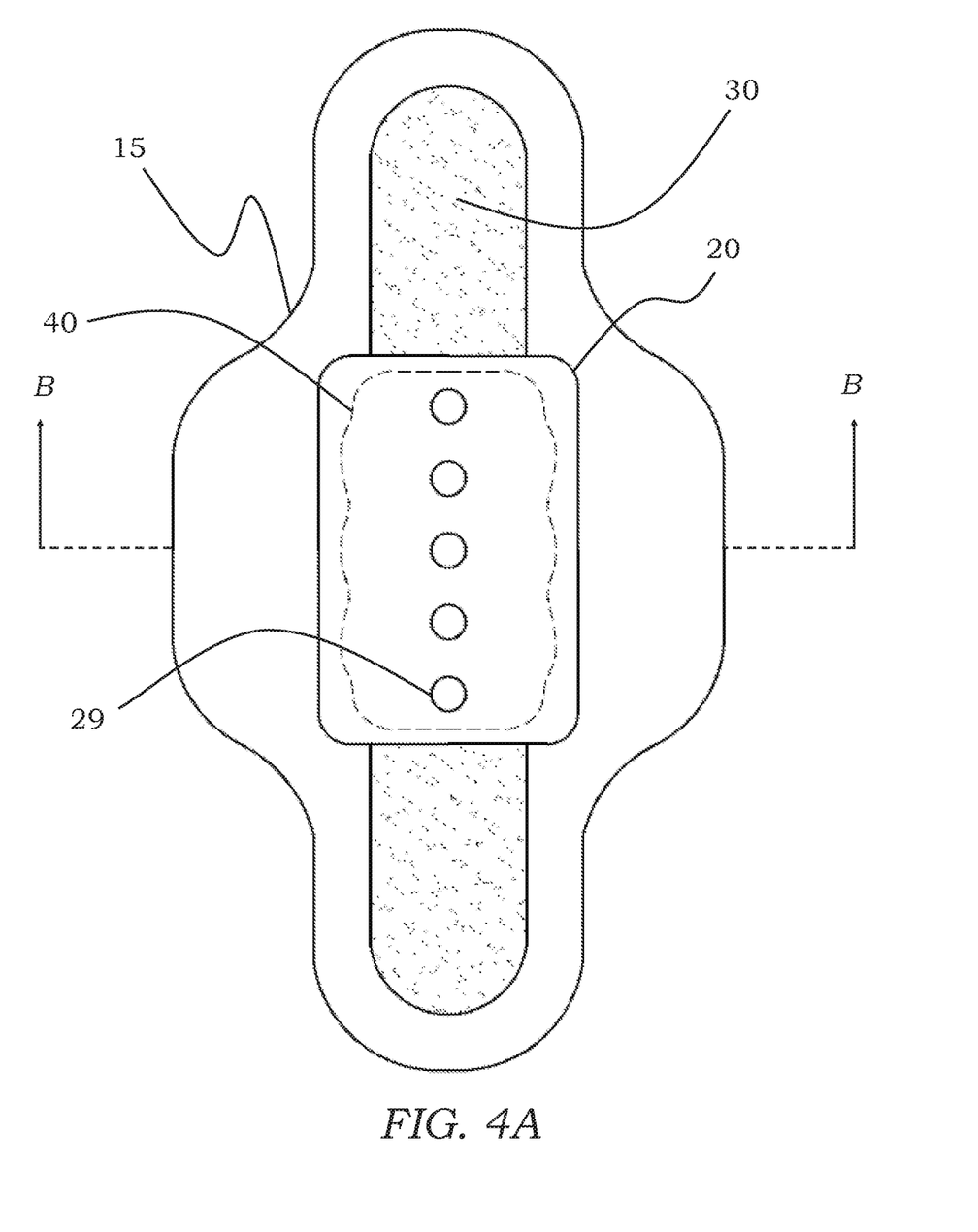
FIG. 4A depicts a top view of a sanitary device adhered to a panty liner.
Figure 4B:
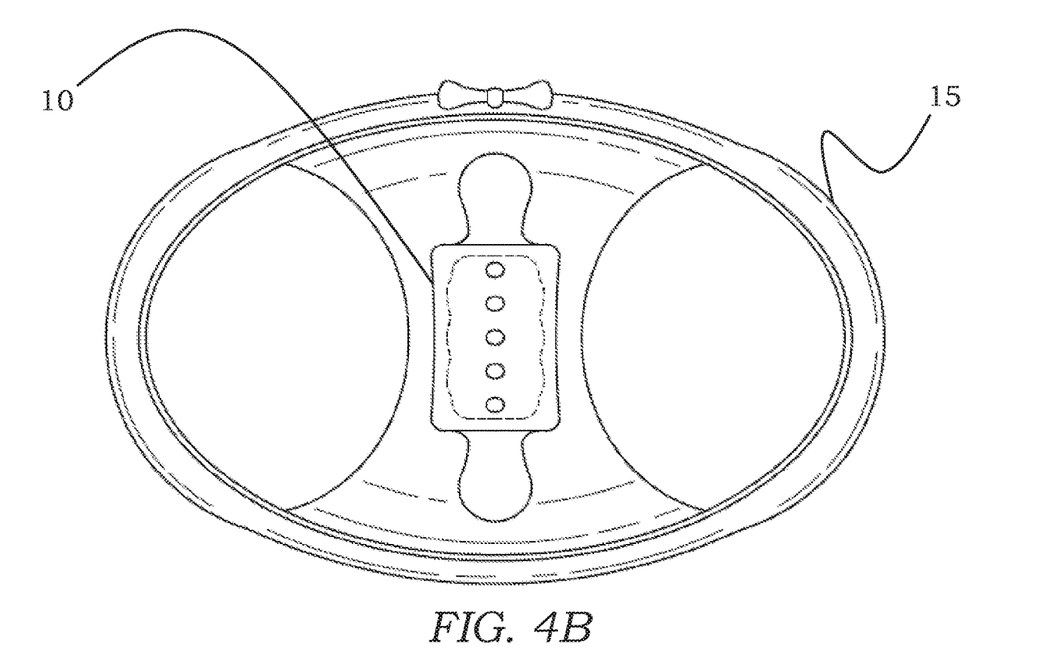
FIG. 4B depicts a top view of a sanitary device adhered to underwear.
Figure 4C:
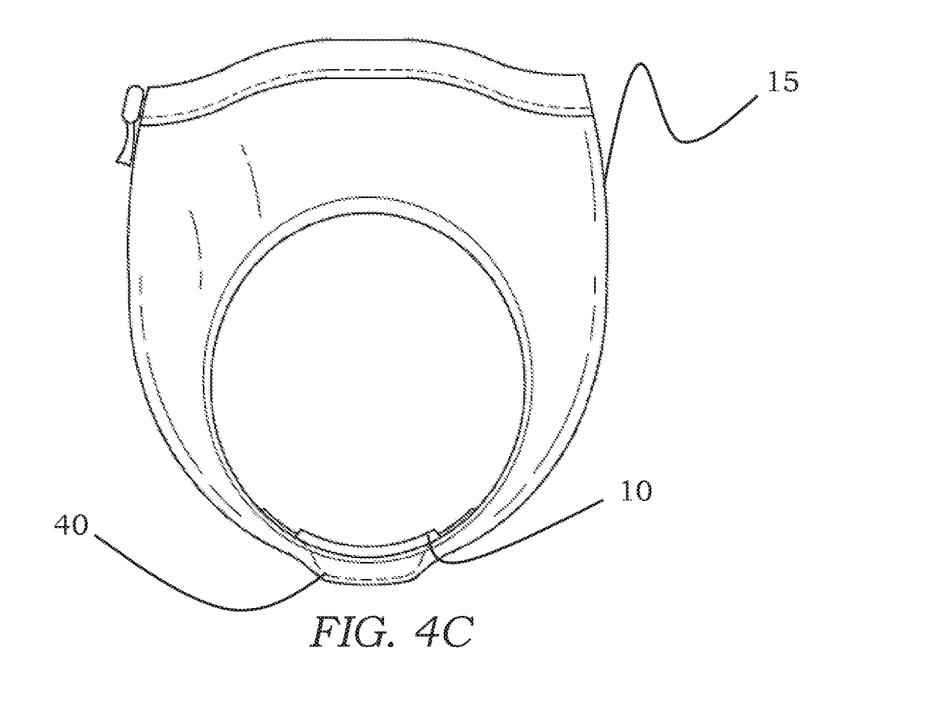
FIG. 4C depicts a side view of an embodiment of a sanitary device adhered to underwear.

Now referring to FIG. 4A, sanitary device 10 is coupled to conventional sanitary device 15—especially during times of heavy flow—using adhesive strips 30 to provide triple protection against leakage and store menstrual fluid discharge away from the opening of the vagina. During periods of lighter flow, sanitary device 10 is directly attached to underwear, panty-liners, incontinence pads. In an embodiment, sanitary device 10 may be used without the need for conventional sanitary device 15 and coupled directly to the epidermis of the wearer. Additional embodiments of sanitary device 10 are contemplated in which sanitary device 10 may be used as an emergency urination bag for adult males, females, and children when a restroom is not readily accessible as depicted in FIGS. 4B and 4C.

Figure 5:
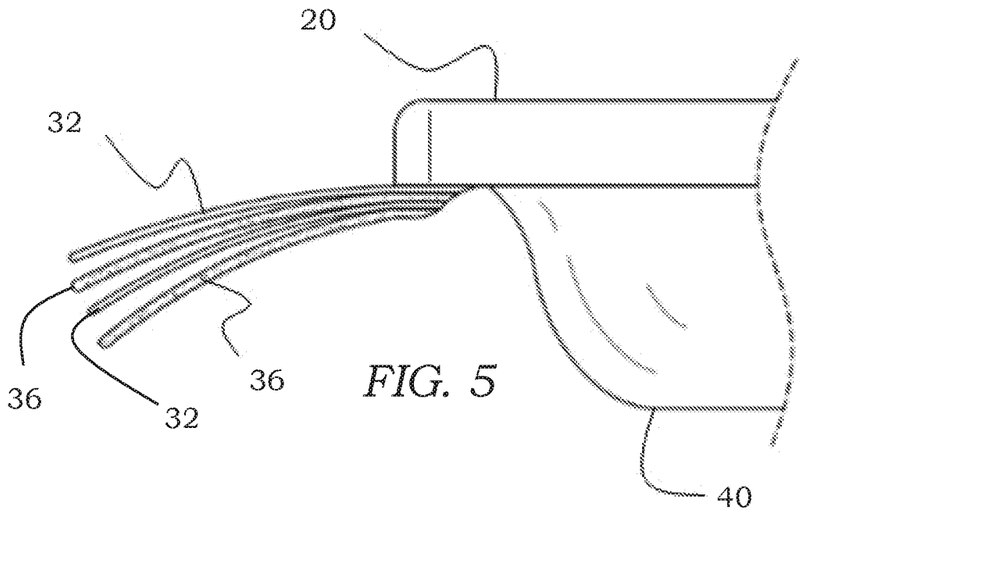
FIG. 5 depicts a close-up side view of a portion of a sanitary device. The close-up side view shows the layers of the adhesive strip.
Figure 6:
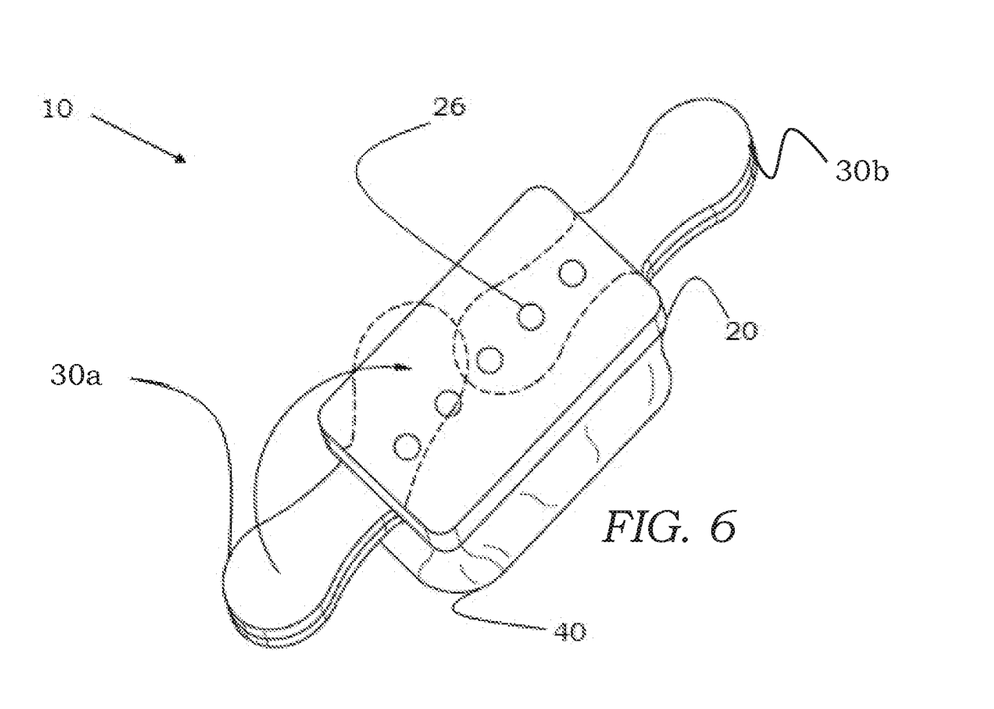
FIG. 6 depicts an embodiment of a sanitary device with adhesive strips disposed over drainage apertures to prevent leaks during transport, storage, and disposal of a soiled sanitary device.

As depicted in FIGS. 5-6, adhesive strips 30 are disposed in underlying relation to absorbent sponge 20 and include first set of adhesive strips 30*a* and second set of adhesive strips 30*b*. Each of the first set 30*a* and second set 30*b* (see FIG. 6) of adhesive strips have a plurality of adhesive portions 36, each separated by impermeable layer 32. Impermeable layer 32 functions to prevent each adhesive portion 36 from adhering to an adjacent adhesive portion 36. To adhere adhesive strips 30 to either conventional sanitary pad 15 or the epidermis of the wearer, impermeable membrane 32 is removed to expose an adhesive lining on at least a portion of the adhesive strips 30. In an embodiment, sanitary device 10 is coupled to conventional sanitary device 15 (e.g., incontinence underwear) and includes pocket 17 configured to receive collection bag 40, when sanitary device 10 is coupled to conventional sanitary device 15.

To remove sanitary device 10 from conventional sanitary device 15, the user simply pulls up on adhesive strips 30, which in turn detaches from the surface of conventional sanitary device 15. Adhesive strips 30 facilitate the removal of sanitary device 10 from conventional sanitary device 15 without contacting the soiled portion of collection bag 40. To prevent fluids from leaking from collection bag 40 during storage, adhesive strips 30 may be disposed over drainage aperture 29, as shown in FIG. 6. After removal, soiled collection bag 40 is easily stored and placed in an opaque storage bag for disposal in the garbage or a purse to carry home for washing and re-use (e.g., for cost or environmental reasons).

Sanitary device 10 is reused by washing absorbent sponge 20 and collection bag 40 during the cleaning process. When collection bag 40 and absorbent sponge 20 are cleaned, impermeable layer 16 prevents the adhesive from being washed away from adhesive portion 36. After washing, absorbent sponge 20 is then re-laced with salt, alcohol, and/or an odor-masking compound. These products are usually stored in most homes or easily purchased at a local supermarket and drug store.

To re-lace the absorbent sponge 20 with salt, the absorbent sponge is soaked or sprayed with a solution containing salt water or saline until absorbent sponge 20 is saturated with the solution. Absorbent sponge 20 is then dried to evaporate the water from the solution. To re-lace absorbent sponge 20 with alcohol, absorbent sponge 20 is soaked or sprayed with a solution containing the alcohol until absorbent sponge 20 is saturated with the solution. Absorbent sponge 20 is then dried to evaporate the water from the solution. In an embodiment, the alcohol may be isopropyl alcohol. To re-lace absorbent sponge 20 with an odor-masking compound, absorbent sponge 20 is soaked or sprayed with a solution containing odor-masking compound until absorbent sponge 20 is saturated with the solution. Absorbent sponge 20 is then dried to evaporate the water from the solution. In an embodiment, the odor-masking compound may be sodium bicarbonate or another odor-masking compound. Further, sodium bi-carbonate aids in the balancing of the pH level of female genitals. Because absorbent sponge 20 is laced with odor-masking compound 34, absorbent sponge 20 does not emit an odor or an odor given off by absorbent sponge 20 is otherwise minimized during storage, disposal, and transport.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A reusable osmotic sanitary collection bag for use in absorbing a fluid discharged from a user, the reusable osmotic sanitary collection bag comprising:
    an absorbent sponge having a first surface, a second surface, and a body extending therebetween, the body including a plurality of drainage apertures extending from the first surface to the second surface, wherein an amount of salt is infused within the absorbent sponge and configured to facilitate, via osmosis, movement of the fluid discharged from the user to a collection bag;

the collection bag disposed in underlying relation to the absorbent sponge and secured thereto using an adhesive, wherein a reservoir is disposed within the collection bag, the reservoir being extended away from the second surface of the sponge, whereby the fluid discharged from the user is absorbed by the absorbent sponge and flows through the plurality of drainage apertures into the reservoir of the collection bag;

a first plurality of adhesive strips disposed in underlying relation to the absorbent sponge and extending away from a first end of the absorbent sponge at a predetermined distance;

a second plurality of adhesive strips disposed in underlying relation to the absorbent sponge and extending away from a second end of the absorbent sponge at the predetermined distance;

wherein the first plurality of adhesive strips, the second plurality of adhesive strips, or both comprise an impermeable layer disposed between each strip, the impermeable layer being configured to facilitate the separation of each strip from one another; and wherein when at least one of the absorbent sponge, the reservoir, or both of the collection bag are cleaned for reuse, the impermeable layer is configured to prevent at least a portion of an adhesive of the first plurality of adhesive strips, the second plurality of adhesive strips, or both from being removed.

2. The reusable osmotic sanitary collection bag of claim 1, wherein the first and the second pluralities of adhesive strips include a dermal adhesive configured to removably adhere the osmotic sanitary collection bag to the epidermis of the user.

3. The reusable osmotic sanitary collection bag of claim 1, wherein a surface is a first surface of a conventional sanitary device, such that the osmotic sanitary collection bag is disposed in overlying relation to the conventional sanitary device.

4. The reusable osmotic sanitary collection bag of claim 1, wherein the body of the absorbent sponge comprises at least one protrusion at least partially disposed within the collection bag, whereby the at least one protrusion maintains an open configuration of the reservoir in the collection bag, thereby facilitating intake of the discharged fluid into the reservoir of the collection bag.

5. The reusable osmotic sanitary collection bag of claim 1, wherein the absorbent sponge is infused with an amount of isopropyl alcohol and configured to kill bacteria and yeast cells.

6. The reusable osmotic sanitary collection bag of claim 1, wherein the absorbent sponge is infused with an amount of an odor-masking substance and configured to mask an odor from the fluid.

7. The reusable osmotic sanitary collection bag of claim 1, further comprising a semi-permeable membrane disposed in overlying relation to the absorbent sponge, wherein the semi-permeable membrane is configured to prevent the salt-infused within the absorbent sponge from contacting the epidermis of a user while permitting passage of the fluid through the semi-permeable membrane.

8. The reusable osmotic sanitary collection bag of claim 7, wherein the semi-permeable membrane further includes a slit disposed parallel to a longitudinal axis extending from the first end to the second end of the sponge, wherein the slit extends at least twenty-five (25) percent of the length of the sponge, whereby the slit is configured to allow passage of larger particles through the semi-permeable membrane and into the drainage apertures of the sponge.

9. An reusable osmotic sanitary collection bag for use in absorbing a fluid discharged from a user, the reusable osmotic sanitary collection bag comprising:

an absorbent sponge having a first surface, a second surface, and a body extending therebetween, the body including a plurality of drainage apertures extending from the first surface to the second surface, wherein the absorbent sponge includes an amount of salt-infused within the absorbent sponge and configured to facilitate, via osmosis, movement of the fluid discharged from the user to a collection bag;

the collection bag disposed in underlying relation to the absorbent sponge and secured thereto using an adhesive, wherein a reservoir is disposed within the collection bag, the reservoir being extended away from the second surface of the sponge, whereby the fluid discharged from the user is absorbed by the absorbent sponge and flows through the plurality of drainage apertures into the reservoir of the collection bag;

a first plurality of adhesive strips disposed in underlying relation to the absorbent sponge and extending away from a first end of the absorbent sponge at a predetermined distance;

a second plurality of adhesive strips disposed in underlying relation to the absorbent sponge and extending away from a second end of the absorbent sponge at the predetermined distance;

wherein the first plurality of adhesive strips, the second plurality of adhesive strips, or both comprise an impermeable layer disposed between each strip, the impermeable layer being configured to facilitate the separation of each strip from one another;

wherein when at least one of the absorbent sponge and the reservoir of the collection bag are cleaned for reuse, the impermeable layer prevents at least a portion of an adhesive of at least one of the first and second plurality of adhesive strips from being removed; and wherein the body of the absorbent sponge comprises at least one protrusion at least partially disposed within the collection bag, whereby the at least one protrusion maintains an open configuration of the reservoir in the collection bag, thereby facilitating intake of the discharged fluid into the reservoir of the collection bag.

10. The reusable osmotic sanitary collection bag of claim 9, further comprising a semi-permeable membrane disposed in overlying relation to the absorbent sponge, wherein the semi-permeable membrane is configured to prevent the salt-infused within the absorbent sponge from contacting the vagina while permitting passage of the fluid through the semi-permeable membrane.

11. The reusable osmotic sanitary collection bag of claim 9, wherein the osmotic sanitary collection bag is disposed in overlying relation to a conventional sanitary device.

12. The reusable osmotic sanitary collection bag of claim 9, wherein the absorbent sponge is infused with an amount of isopropyl alcohol and configured to kill bacteria and yeast cells.

13. The reusable osmotic sanitary collection bag of claim 9, wherein the absorbent sponge is infused with an amount of sodium bicarbonate, wherein the sodium bicarbonate is configured to mask the odor of the fluid discharged during menstruation.

14. The reusable osmotic sanitary collection bag of claim 9, wherein at the first plurality of adhesive strips, the second plurality of adhesive strips, or both are configured to be removably affixed to at least one of the plurality of drainage apertures, whereby subsequent to the reservoir of the collection bag accumulating a predetermined amount of the discharged fluid, at least one of the plurality of drainage apertures is temporarily sealed by the first plurality of adhesive strips, the second plurality of adhesive strips, or both, thereby preventing leakage of the discharged fluid from the reservoir of the collection bag during removal from the user for cleaning, disposal, or both of the osmotic sanitary collection bag.

15. A reusable osmotic sanitary collection bag for use in absorbing a fluid discharged from a user, the reusable osmotic sanitary collection bag comprising:

an absorbent sponge having a first surface, a second surface, and a body extending therebetween, the body including a plurality of drainage apertures extending from the first surface to the second surface, wherein an amount of salt is infused within the absorbent sponge and configured to facilitate, via osmosis, movement of the fluid discharged from the user to a collection bag;

the collection bag disposed in underlying relation to the absorbent sponge and secured thereto using an adhesive, wherein a reservoir is disposed within the collection bag, the reservoir being extended away from the second surface of the sponge, whereby the fluid discharged from the user is absorbed by the absorbent sponge and flows through the plurality of drainage apertures into the reservoir of the collection bag;

a semi-permeable membrane disposed in overlying relation to the absorbent sponge and configured to prevent the salt-infused within the absorbent sponge from contacting the vagina while permitting passage of the fluid through the semi-permeable membrane;

a first plurality of adhesive strips disposed in underlying relation to the absorbent sponge and extending away from a first end of the absorbent sponge at a predetermined distance;

a second plurality of adhesive strips disposed in underlying relation to the absorbent sponge and extending away from a second end of the absorbent sponge at the predetermined distance;

wherein the first plurality of adhesive strips, the second plurality of adhesive strips, or both comprise an impermeable layer disposed between each strip, the impermeable layer being configured to facilitate the separation of each strip from one another;

wherein upon the discharge of a fluid by a user, the fluid is absorbed by the absorbent sponge and received within the reservoir of the collection bag;

wherein the body of the absorbent sponge comprises at least one protrusion at least partially disposed within the collection bag, whereby the at least one protrusion maintains an open configuration of the reservoir in the collection bag, thereby facilitating intake of the discharged fluid into the reservoir of the collection bag; and wherein the impermeable layer is configured to be removably affixed to at least one of the first and second plurality of adhesive strips, whereby when at least one of the absorbent sponge and the reservoir of the collection bag are cleaned for reuse, the impermeable layer prevents at least a portion of an adhesive of at least one of the first and second plurality of adhesive strips from being removed.

16. The reusable osmotic sanitary collection bag of claim 15, wherein the absorbent sponge further includes an amount of alcohol configured to kill bacterial and yeast cells and an amount of an odor-masking substance configured to mask an odor of the fluid discharged from the wearer.

17. The reusable osmotic sanitary collection bag of claim 15, wherein the first and second pluralities of adhesive strips include a dermal adhesive used to removably adhere the osmotic sanitary collection bag to the epidermis of the user.

18. The reusable osmotic sanitary collection bag of claim 1, wherein the collection bag comprises a discharge mechanism, the discharge mechanism having an opening extending between an interior of the reservoir and an exterior of the collection bag, wherein the discharge mechanism is configured to encompass a stopper, whereby the stopper is configured to inhibit transfer of fluid or larger particles through the discharge mechanism when encompassed by the discharge mechanism.

* * * * *